US009622930B2

(12) United States Patent
Sands

(10) Patent No.: US 9,622,930 B2
(45) Date of Patent: Apr. 18, 2017

(54) ERGO-MALE URINAL

(71) Applicant: Patricia Carol Sands, Arlington, VA (US)

(72) Inventor: Patricia Carol Sands, Arlington, VA (US)

(*) Notice: Subject to any disclaimer, the term of this patent is extended or adjusted under 35 U.S.C. 154(b) by 149 days.

(21) Appl. No.: 14/273,619

(22) Filed: May 9, 2014

(65) Prior Publication Data

US 2015/0320628 A1  Nov. 12, 2015

(51) Int. Cl.
 A47K 11/00 (2006.01)
 A61G 9/00 (2006.01)
 A61F 5/453 (2006.01)

(52) U.S. Cl.
 CPC .............. *A61G 9/006* (2013.01); *A61F 5/453* (2013.01)

(58) Field of Classification Search
 CPC .......... A61G 9/006; A61F 5/44; A61F 5/4556
 USPC ................................. 4/144.1–144.4; D24/122
 See application file for complete search history.

(56) References Cited

U.S. PATENT DOCUMENTS

| D213,408 S | * | 2/1969 | Brodsky | ...................... D24/122 |
| 4,901,375 A | * | 2/1990 | Dahlgren | ............... A61G 9/006 |
| | | | | 224/148.2 |
| 6,026,519 A | * | 2/2000 | Kaluza | ................... A61G 9/006 |
| | | | | 4/144.1 |
| 6,109,441 A | * | 8/2000 | Anderson | ............. A61G 9/006 |
| | | | | 206/438 |
| 6,460,199 B1 | * | 10/2002 | Sands | .................... A61G 9/006 |
| | | | | 4/144.1 |
| D685,465 S | * | 7/2013 | Reda | ........................... D24/122 |
| 2009/0158511 A1 | * | 6/2009 | Maze | ..................... A47K 11/12 |
| | | | | 4/144.1 |

* cited by examiner

*Primary Examiner* — Paul R Durand
*Assistant Examiner* — Nicholas Ros
(74) *Attorney, Agent, or Firm* — Michael J. Foycik, Jr.

(57) ABSTRACT

A urinal includes a body that has a front wall, a rear wall, opposed side walls, a bottom wall and a top wall. The body has a front portion having an opening and has a rear portion. The body has an opening in the front wall portion adapted for entry of a male body portion. The front wall portion has an S-shaped portion forming a ridge extending below said opening. A ledge is formed by part of the S-shaped portion to form a support for the male body portion entered into the opening. The rear portion is higher than the front portion such that the body is tapered in a directon from back to front. The body also tapers in width from back to front, so that it is adapted to fit comfortably between the thighs of a user.

8 Claims, 10 Drawing Sheets

ERGO-MALE URINAL

CROSS REFERENCE TO RELATED APPLICATIONS

Not applicable.

STATEMENT REGARDING FEDERALLY SPONSORED RESEARCH OR DEVELOPMENT

Not applicable.

FIELD OF THE INVENTION

The present invention relates to a male urinal, which is especially for use by a person in a wheelchair or bed.

BACKGROUND OF THE INVENTION

Portable urinals are known in the art. Such urinals can take the form of simple bowls or containers, or may have spouts or the like.

It is, however, a problem in the art to provide a urinal which provides more freedom and a more hygienic environment for a person seated in a wheelchair or in a bed.

It is a further problem in the art to provide a urinal which stays in place without being held, and is resistant to urine spillage.

It is another problem in the art to provide a urinal which can be comfortably used and is ergonomically shaped.

SUMMARY OF THE INVENTION

From the foregoing, it is seen that it is a problem in the art to provide a device meeting the above requirements. According to the present invention, a device is provided which meets the aforementioned requirements and needs in the prior art. Specifically, the device according to the present invention provides a male urinal that is ergonomically shaped, resistant to spills, and stabilized during use.

The ergononimcally shaped male urinal of the present invention provides freedom and a hygienic environment for a person in a wheelchair or bed. The urinal is shaped so it stays in place without being held, is resistant to spillage, and can be comfortably used for hours at a time. In one preferred embodiement, the urinal includes a relatively soft, translucent or clear plastic body with rounded edges, and is shaped so it fits close to the body of the user and under the thighs of the user. It thereby uses the pressure of the thighs of the user to hold it in place. The urinal has an S-shaped front section, conforming with the male anatomy, allowing a closer and more comfortable fit for male users.

The urinal of the present invention has a shape that is generally tapered downward in a direction from rear to front, and has a wide rear surface forming a base so that it can be stood on its end. It also includes a handle that extends from to top of a spout-like portion of the urinal, which can conveniently be used to hang the urinal from a beds or wheelchairs.

The urinal further includes a Day-Glo™ type (e.g. having very bright or fluorescent coloring) of lid, which can glow at night and which is irridescent and/or brightly colored for good visibility in daylight and in well-lit environments.

The S-shaped portion of the urinal of the present invention provides a ledge for supporting the male body portion inside the urinal interior without letting it enter a pool of liquid inside.

Further, the base of the urinal has ribs for added slip resistance. It also uses the pressure of the thighs of the user to hold it in place.

The S-shaped front portion of the urinal conforms with the male anatomy, allowing a closer and more comfortable fit for male users. The aforementioned ledge portion also helps the urinal to retain liquid without spilling even when it is tilted forward. Thus, the urine cannot be spilled backward into the body of the user unless it is tilted to an extreme angle or filled to over its capacity.

The opening of the urinal also serves as a pouring spout formed along the forward and upper portion of the opening in the receptacle area. The emptying or pouring can for example be performed by rotating the urinal backwards, front end over the rear end thereof. The urinal body is rounded for ergonomic purposes, as well as for manufacturing purposes.

The urinal of the present invention is formed of translucent soft plastic. It can, however, also be made of clear plastic. And, the body of the urinal can be formed with markings in liquid measure intervals such as milliliters (ml.) for easy measuring, for use in keeping urine output records. The urinal is provided with a wide opening so that it can be disinfected with ease.

Many other applications exist for the urinal of the present invention, including for use in trucks, cars, airplanes, subways, boats, camping, and for recreational outings.

Other objects and advantages of the present invention will be more readily apparent from the following detailed description when read in conjunction with the accompanying drawings.

DETAILED DESCRIPTION OF THE INVENTION

Figure 1:
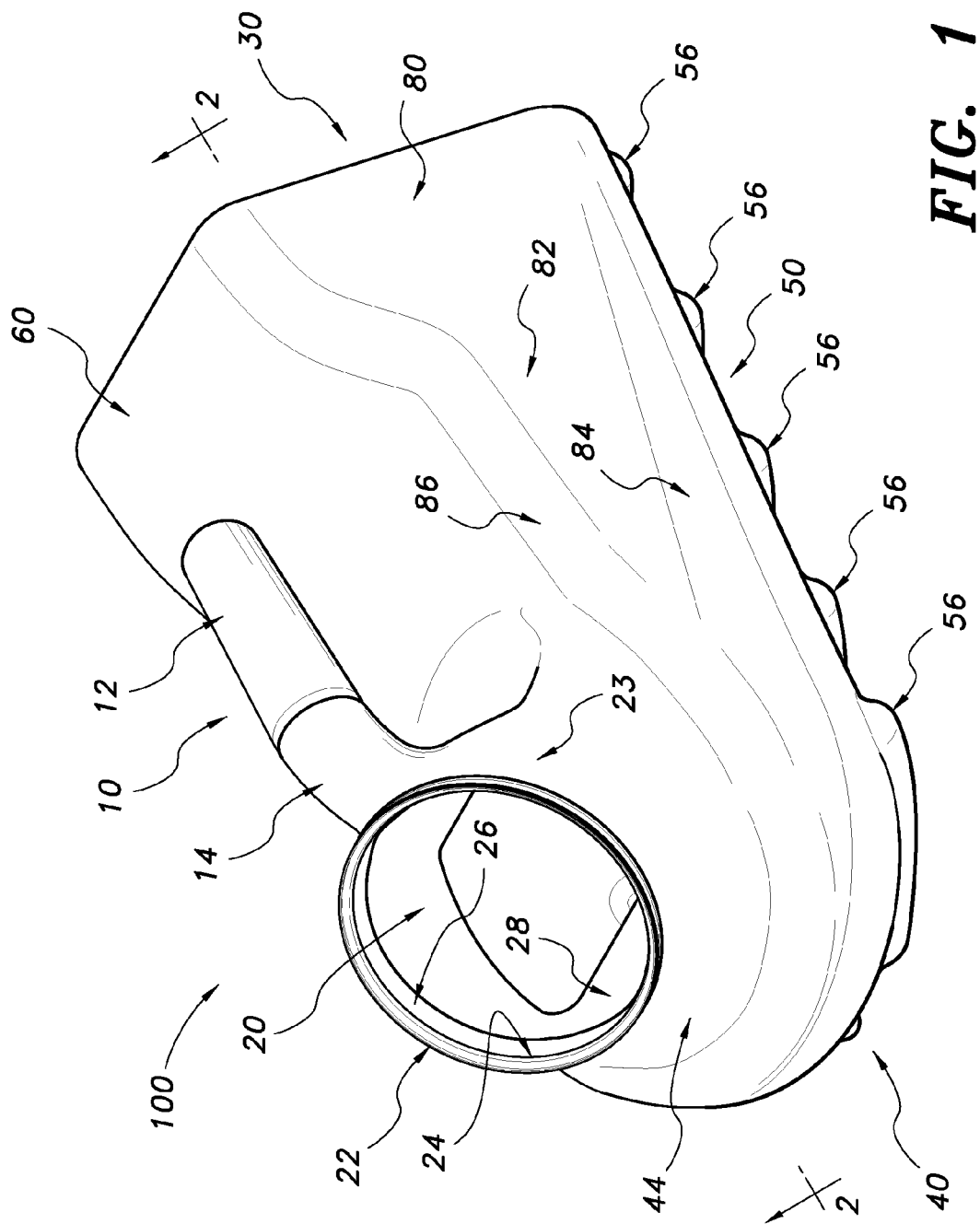
FIG. 1 is a perspective view of an ergo-male urinal according to the present invention, showing a top portion, a front portion, and one side portion.

FIG. 1 is a perspective view of an ergo-male urinal 100 according to the present invention, showing a top portion 60, a front portion 40, and a side wall 80. The ergo-male urinal 100 of FIG. 1 also includes a handle 10, a bottom wall 50, a rear wall 30, and an opening 20 which communicates with a hollow interior of the ergo-male urinal 100 which serves as a receptacle portion to contain liquid.

The opening 20 is bounded by a rim portion 22, a ridge portion 24, a wall portion 26, and a lip portion 28.

The outside region near the opening 20 of the ergo-male urinal 100 includes a curved wall portion 44 and a connecting wall portion 23 which supports a handle connecting portion 14 which in turn is connected to a body portion 12 of the handle 10. The handle 10 includes the portions 12 and 14.

As seen in FIG. 1, the side wall 80 includes a wall portion 82, and a connecting wall portion 84 which extends to the bottom wall 50, and a connecting wall portion 86 which extends to the top portion 60. The bottom wall 50 has a plurality of rib portions 56 to improve gripping and improve stability.

Figure 2:
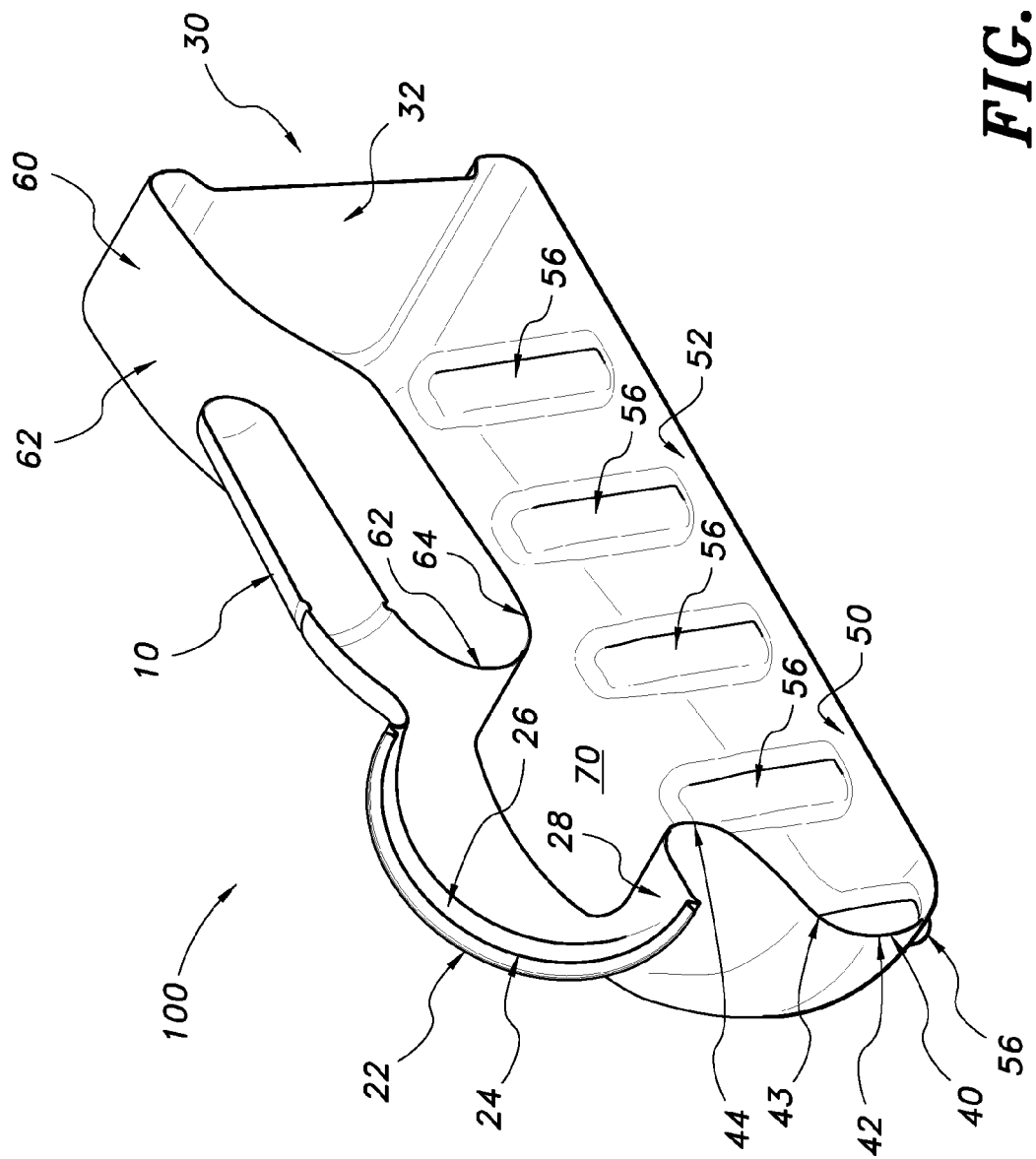
FIG. 2 is a sectional view taken along a central longitudinal plane of the ergo-male urinal of FIG. 1, according to the present invention.

FIG. 2 is a sectional view taken along a central longitudinal plane (indicated by line 2-2 of FIG. 1) of the ergo-male urinal 100 of FIG. 1. The numerals corresponding to those of FIG. 1 are as described hereinabove. In this view, the concave curved shape of the curved wall portion 44 is shown, as well as the lip portion 28. The lip portion 28 forms a ledge to support the male anatomy entered into the opening 20, so that it does not enter into the liquid in the urinal 100.

FIG. 2 additionally shows a lowermost front wall portion 42 connected with the bottom 50, a curved wall portion 43 connecting the wall portion 42 with the curved wall portion 44. FIG. 2 thereby shows clearly an S-shaped front portion formed by the wall portions 43, 44, and 28.

FIG. 2 also shows a relatively flat wall body portion 32 of the rear wall 30, and a relatively flat wall body portion 52 of the bottom wall 50. Additionally, FIG. 2 shows a main wall portion 64 of the top portion 60 as well as a connecting wall portion 62 which connects the wall portion 64 with the handle 10. This view also shows a side wall 70, which is the counterpart of the side wall 80 shown in FIG. 1. The other half of the urinal 100 is a mirror image of the half shown in FIG. 2.

The ergononimcally shaped male urinal 100 of the present invention provides freedom and a hygienic environment for a person in a wheelchair or bed. The urinal 100 is shaped so it stays in place without being held, is resistant to spillage, and can be comfortably used for hours at a time. In one preferred embodiment, the urinal 100 includes a relatively soft, translucent or clear plastic body with rounded edges, and is shaped so it fits close to the body of the user and under the thighs of the user. It thereby uses the pressure of the thighs of the user to hold it in place. The urinal 100 has the S-shaped front section elements 43, 44, 28 as shown in FIG. 2, conforming with the male anatomy, allowing a closer and more comfortable fit for male users.

The urinal 100 of the present invention has a shape that is generally tapered downward in a direction from rear to front, and has a wide rear surface forming a base so that it can be stood on its end. It also includes a handle that extends from to top of a spout-like portion of the urinal 100, which can conveniently be used to hang the urinal 100 from a beds or wheelchairs.

The urinal 100 further includes a Day-Glo™ type (e.g. having very bright or fluorescent coloring) of lid 202 (shown in FIG. 10), which can glow at night and which is irridescent and/or brightly colored for good visibility in daylight and in well-lit environments.

The aforementioned S-shaped portion of the urinal 100 of the present invention provides a ledge or lip portion 28 for supporting the male body portion inside the urinal interior without letting it enter a pool of liquid inside.

Further, the base 50 of the urinal 100 has ribs 56 for added slip resistance. It also uses the pressure of the thighs of the user to hold it in place.

The S-shaped front portion of the urinal 100 conforms with the male anatomy, allowing a closer and more comfortable fit for male users. The aforementioned ledge portion 28 also helps the urinal 100 to retain liquid without spilling even when it is tilted forward. Thus, the urine cannot be spilled backward into the body of the user unless the urinal 100 is tilted to an extreme angle or filled to over its capacity.

The opening 20 of the urinal 100 also serves as a pouring spout formed along the forward and upper portion of the opening in the receptacle area. The emptying or pouring can for example be performed by rotating the urinal 100 backwards, front end over the rear end thereof. The urinal body is rounded for ergonomic purposes, as well as for manufacturing purposes.

The urinal 100 of the present invention is preferably formed of translucent soft plastic. It can, however, also be made of clear plastic. And, the body of the urinal can be formed with markings in liquid measure intervals such as milliliters (ml.) for easy measuring, for use in keeping urine output records.

The urinal 100 is provided with a wide opening (20) so that it can be disinfected with ease.

Many other applications exist for the urinal of the present invention, including for use in trucks, cars, airplanes, subways, boats, camping, and for recreational outings.

The benefits of the urinal 100 of the present invention include providing a safe and sanitary alternative to use of catheters which might precipitate an internal urinary tract infection. Another benefit is the decrease in the possibility of bedsores from having the urine spill on the body of the user. Further, there is the benefit of freeing the user from having to hold the urinal in place manually for extended periods of time, and of freeing a caregiver or caretaker from having to hold the urinal in place manually.

The urinal 100 can advantageously be used in bed, and in seats or chairs including wheelchairs. The urinal 100 is reusable and sanitary, and can be used in homes, nursing homes, and hospitals, for example.

Figure 3:
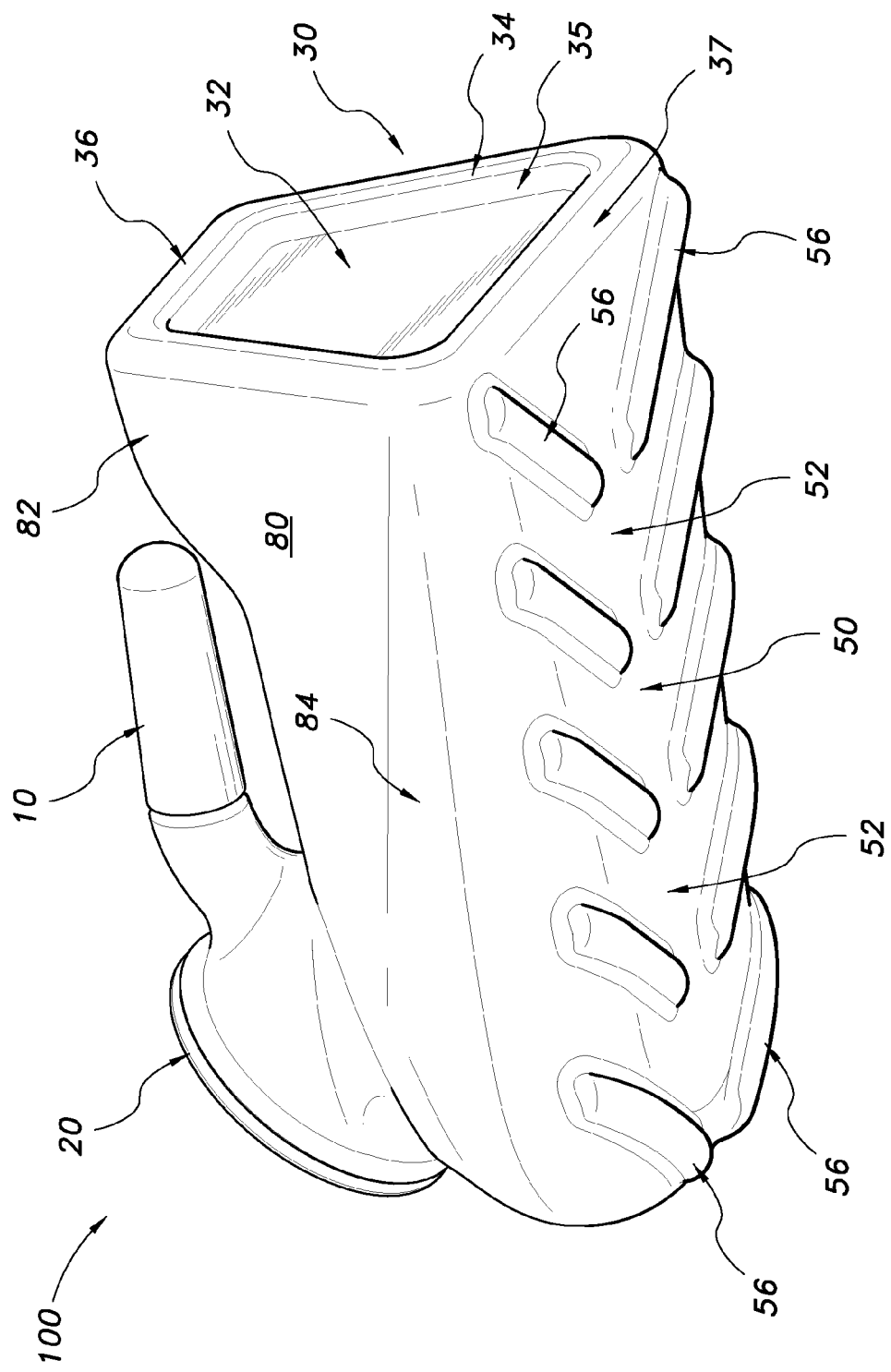
FIG. 3 is another perspective view of the ergo-male urinal of FIG. 1 showing a bottom portion, a rear portion, and the side portion.

FIG. 3 is another perspective view of the ergo-male urinal 100 of FIG. 1 showing the bottom wall 50, the rear wall 30, and the side wall 80. The rear wall 30 includes a generally trapezoidally shaped ledge portion 36, and wall portions 34, 35 connecting the ledge portion 36 with the wall portion 32. A bottom edge 37 is indicated where the rear wall 30 meets the bottom wall 50.

Figure 4:
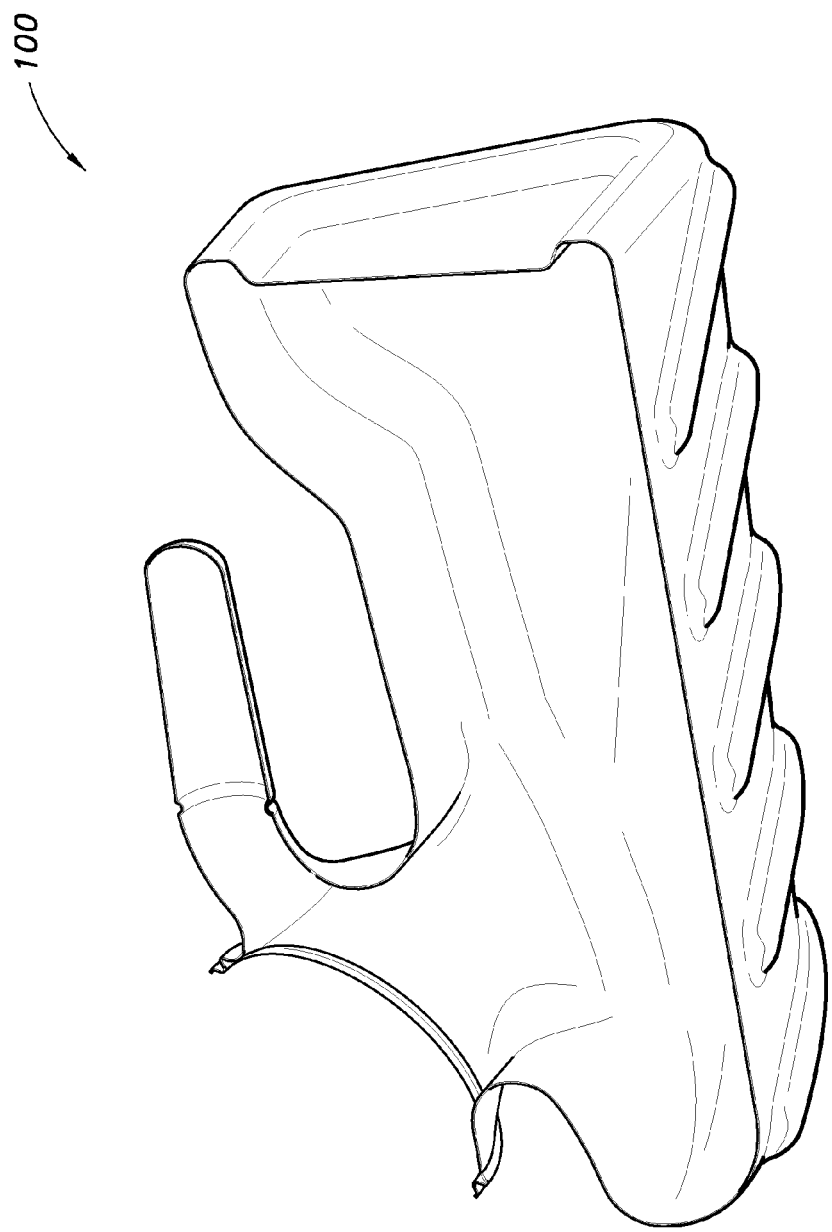
FIG. 4 is a sectonal view taken along a centerline of the ergo-male urinal of FIG. 3.

FIG. 4 is a sectonal view taken along a centerline of the ergo-male urinal 100 of FIG. 3. It shows the curves outlines of the aforementioned elements of the invention, and omits most of the numerals for the sake of clarity.

Figure 5:
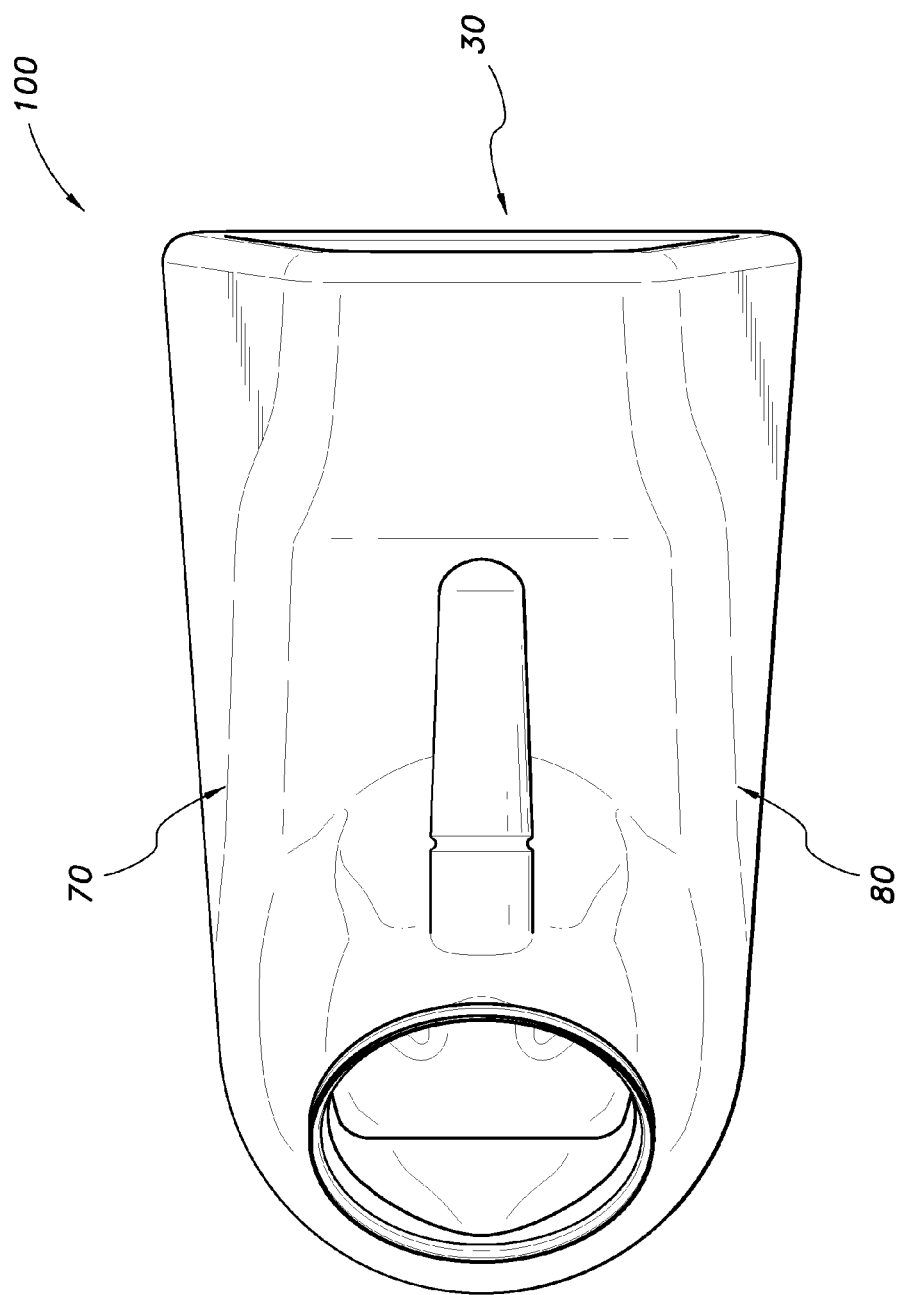
FIG. 5 is a top elevational view of the ergo-male urinal of FIG. 1.

FIG. 5 is a top elevational view of the ergo-male urinal 100 of FIG. 1. This view shows the side walls 70 and 80, and the rear wall 30, as viewed from above.

Figure 6:
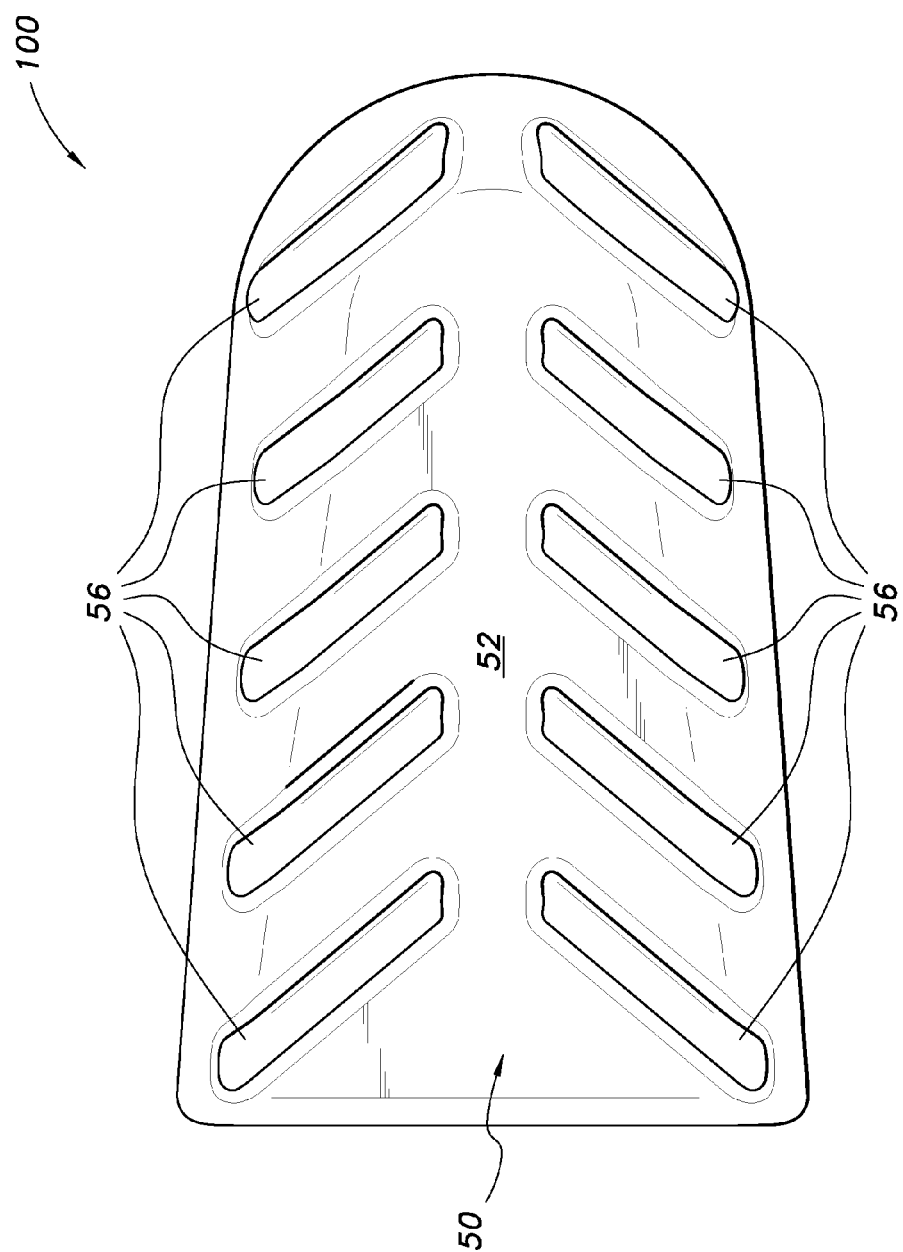
FIG. 6 is a bottom elevational view of the ergo-male urinal of FIG. 1.

FIG. 6 is a bottom elevational view of the ergo-male urinal 100 of FIG. 1, showing the ridges 56, as viewed from below.

Figure 7:
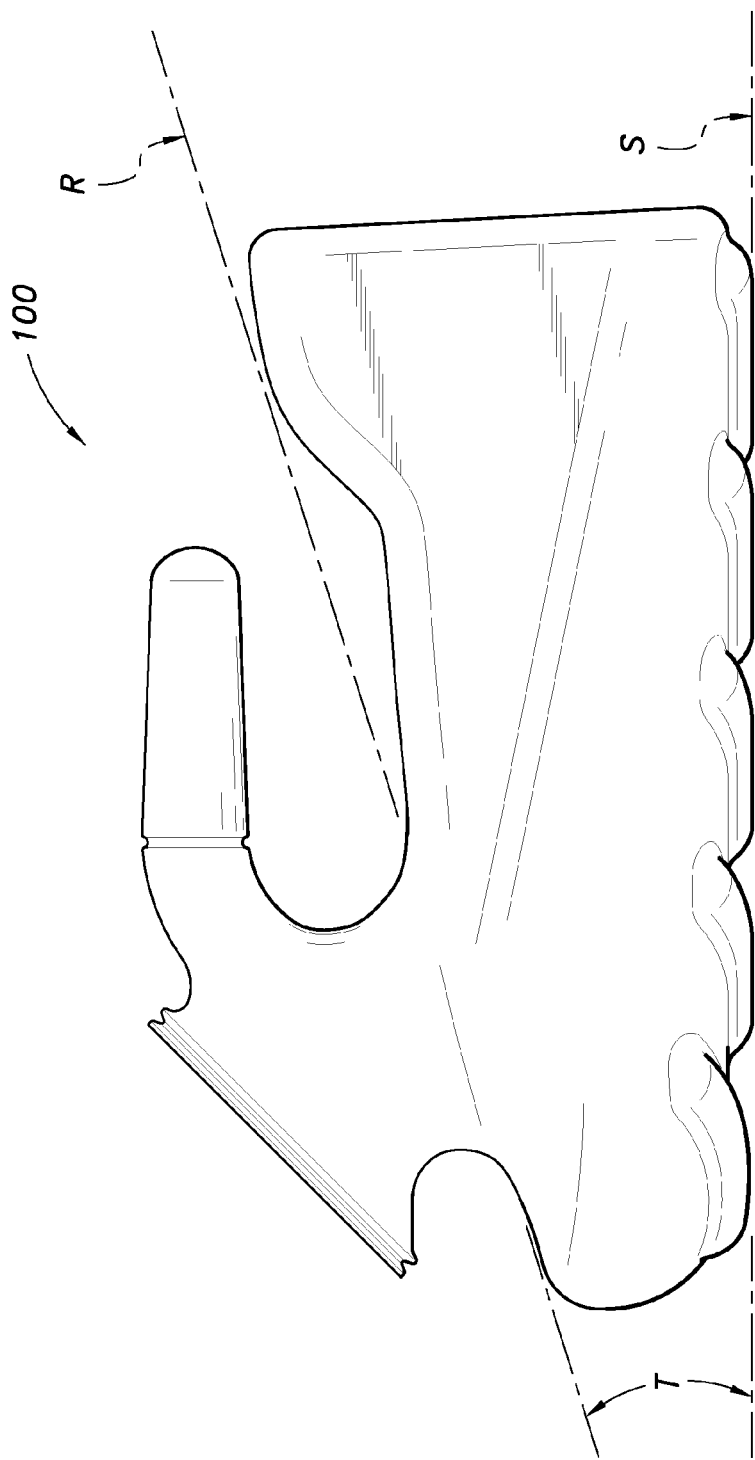
FIG. 7 is a side elevational view of the ergo-male urinal of FIG. 1.

FIG. 7 is a side elevational view of the ergo-male urinal 100 of FIG. 1. In this view, a line marked R generally follows the tapering top portion of the urinal 100 of the present invention, showing that it tapers in a direction downwardly from rear to front. A line marked S is shown paralled to the bottom wall (50). The lines marked R and S meet at an angle, denoted T, as shown in FIG. 7. The angle T is approximately in the range of 15 to 24 degrees.

Figure 8:
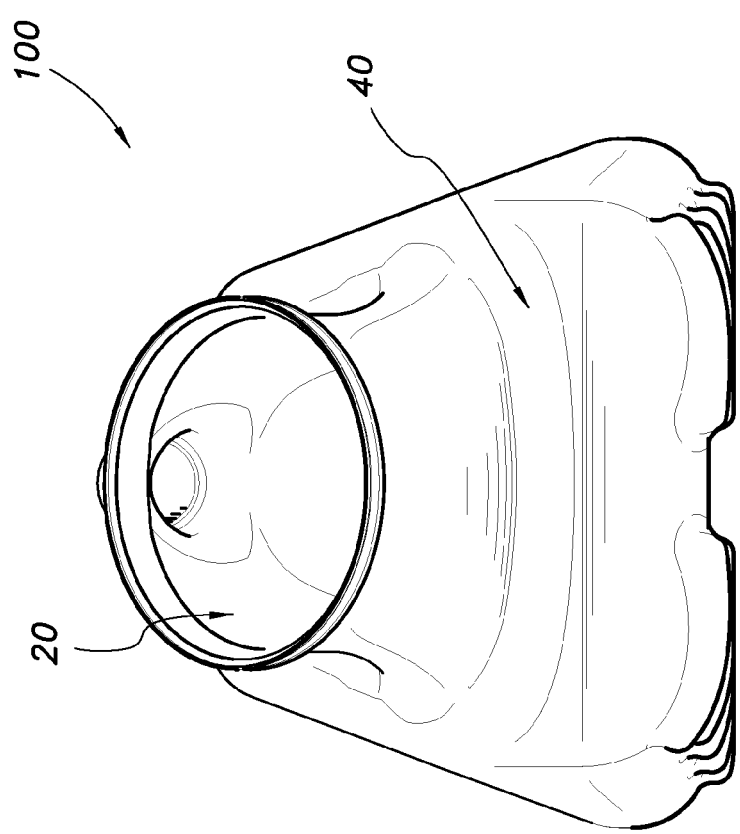
FIG. 8 is a front elevational view of the ergo-male urinal of FIG. 1.

FIG. 8 is a front elevational view of the ergo-male urinal 100 of FIG. 1, showing the front portion 40 and the opening 20.

Figure 9:
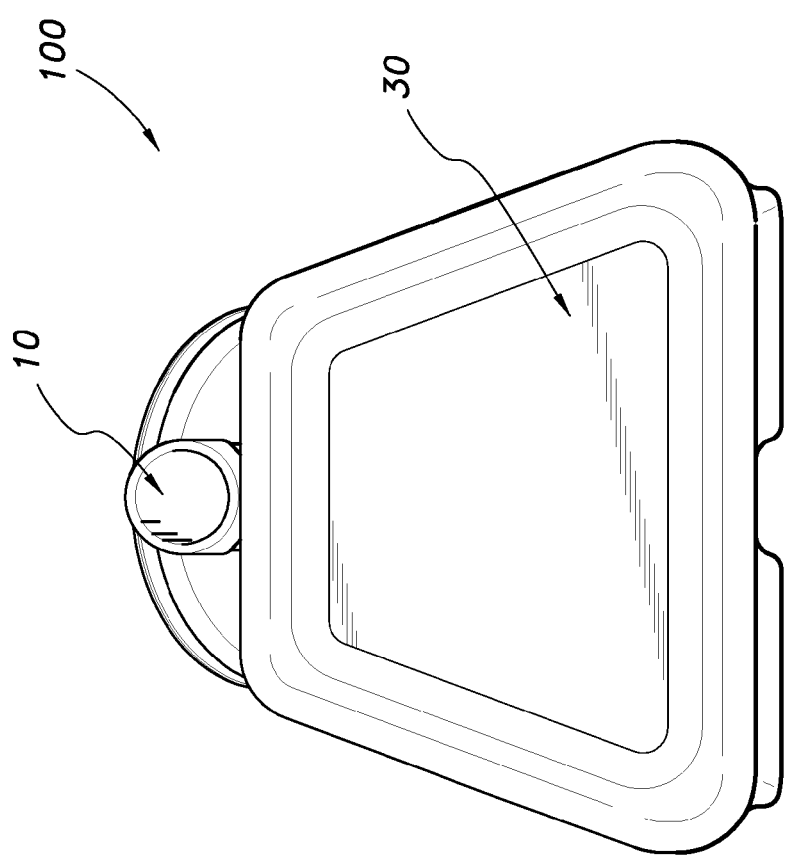
FIG. 9 is a rear elevational view of the ergo-male urinal of FIG. 1.

FIG. 9 is a rear elevational view of the ergo-male urinal 100 of FIG. 1, showing the rear wall 30 and the end portion of the handle 10.

Figure 10:
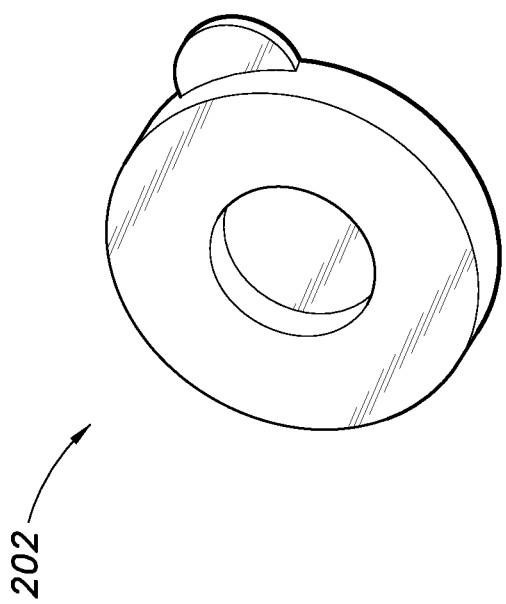
FIG. 10 is a top elevational view of a lid for use with the ergo-male urinal of FIG. 1.

FIG. 10 is a top elevational view of a lid 202 for use in covering the opening 20 of the urinal. The lid 202 is circularly shaped with a projecting tab (unnumbered) for ease of removal. The lid 202 is preferably a snap-on type of lid. In a preferred embodiment, the lid 202 includes a Day-Glo™ type (e.g. having very bright or fluorescent coloring) of material such that it glows in the dark. The lid 202 also can includes a brightly colored Day-Glo™ type (e.g. having very bright or fluorescent coloring) of material for enhanced visibility in daylight and in well-lit environments.

The invention being thus described, it will be evident that the same may be varied in many ways by a routineer in the applicable arts. Such variations are not to be regarded as a departure from the spirit and scope of the invention and all such modifications are intended to be included within the scope of the claims.

What is claimed is:

1. A urinal having a hollow interior forming a urine receptacle for use between thighs of a user, the urinal comprising:

a body having a hollow interior, said body having a front portion, a rear portion having a rear wall, two opposed side walls, a bottom wall, and a top portion having a top wall and a curved portion;

said front portion, said rear wall, said two opposed side walls, said bottom wall, and said top portion bounding said hollow interior of said body, said body being adapted to contain liquid within said hollow interior;

said bottom wall tapering smoothly from said rear wall in a direction toward said front portion;

said top portion including a handle, wherein said curved portion of said top portion supports said handle, and wherein said curved portion of said top portion joins said top wall; and said top wall having a generally flat portion joining an upper edge of said rear wall;

said front portion of said body having an opening in communication with said hollow interior; said front portion of said body having a front wall curving along a generally semicircular arc; said front wall having an S-shaped region, said S-shaped region having a central portion forming a lower part of said S-shaped region wherein said central region bulges outwardly such that it extends beyond said bottom wall as well as above said bottom wall; said S-shaped region of said front wall having an upper portion which curves sharply toward said opening, wherein said upper portion of said front wall then curves upward away from said bottom wall along said opening and then curves sharply outward away from said opening while continuing to rise away from said bottom wall; wherein said opening is bounded on a rear side by curved portion of said top portion, and is bounded on other sides by said upper portion of said S-shaped region of said front wall;

said rear portion being larger than said front portion; and said rear wall of said rear portion having a trapezoidal shape which is largest where said rear wall meets said bottom wall;

said two opposed side walls being connected at their lowermost ends to said bottom wall, said two opposed side walls sloping toward each other in a direction from said bottom wall toward said top wall where they meet said top portion; said two opposed side walls sloping away from each other in a direction from said front portion of said body toward said rear wall; whereby said two opposed side walls are adapted to fit between and partially beneath the thighs of a user;

said opening being adapted for entry of a male body portion; said upper portion of said S-shaped region forming a ledge for resting said male body portion; said opening having a rim portion rising away from said bottom wall in a direction from said upper portion of said S-shaped region toward said rear wall; and wherein said rear portion of said body being at a greater height than said front portion of said body when said body is in use as a urinal.

2. A urinal according to claim 1, wherein said opening comprises a pouring spout portion formed along a forward and upper portion of said aperture, such that emptying and pouring of liquid from within said body is performed by rotating said body in a backwards direction, front end over rear end.

3. A urinal according to claim 1, further comprising a handle connected adjacent said opening and said top wall portion, adapted to serve as a hook to secure said body by hanging.

4. A urinal according to claim 1, wherein said opening is sufficientlywide to allow manual cleaning, such that it is adapted to be disinfected with relative ease.

5. A urinal according to claim 1, wherein said body is composed of a translucent plastic, such that liquid inside said body is visible.

6. A urinal according to claim 1, wherein said body is marked in liquid measure intervals, for use in keeping urine output records.

7. A urinal according to claim 1, further comprising a lid adapted to cover said opening; said lid being composed of material of a type adapted to glow in the dark.

8. A urinal according to claim 7, wherein said lid is additionaly of a flourescent type of material that is colored and has enhanced visibility when view in well lit environments.

* * * * *